(12) United States Patent
Yang et al.

(10) Patent No.: US 7,544,511 B2
(45) Date of Patent: Jun. 9, 2009

(54) STABLE NEURAL STEM CELL LINE METHODS

(75) Inventors: Renji Yang, Silver Spring, MD (US); Karl K. Johe, Potomac, MD (US)

(73) Assignee: Neuralstem Biopharmaceuticals Ltd., College Park, MD (US)

( * ) Notice: Subject to any disclaimer, the term of this patent is extended or adjusted under 35 U.S.C. 154(b) by 200 days.

(21) Appl. No.: 10/047,352

(22) Filed: Jan. 14, 2002

(65) Prior Publication Data
US 2002/0064873 A1  May 30, 2002

Related U.S. Application Data

(63) Continuation of application No. 09/398,897, filed on Sep. 20, 1999, now abandoned, and a continuation-in-part of application No. 09/053,414, filed on Apr. 1, 1998, now abandoned, which is a continuation-in-part of application No. 08/719,450, filed on Sep. 25, 1996, now Pat. No. 5,753,506.

(60) Provisional application No. 60/101,354, filed on Sep. 22, 1998.

(51) Int. Cl.
*C12N 5/08* (2006.01)
*C12N 5/22* (2006.01)

(52) U.S. Cl. .................. 435/368; 435/375; 435/377

(58) Field of Classification Search .............. 435/325, 435/368, 377; 424/93.21
See application file for complete search history.

(56) References Cited

U.S. PATENT DOCUMENTS

| | | |
|---|---|---|
| 5,166,065 A | 11/1992 | Williams et al. |
| 5,340,740 A | 8/1994 | Petitte et al. |
| 5,486,359 A | 1/1996 | Caplan et al. |
| 5,580,777 A | 12/1996 | Bernard et al. |
| 5,589,376 A | 12/1996 | Anderson et al. |
| 5,654,183 A | 8/1997 | Anderson |
| 5,672,499 A | 9/1997 | Anderson et al. |
| 5,693,482 A | 12/1997 | Anderson et al. |
| 5,750,376 A | 5/1998 | Weiss et al. |
| 5,753,505 A | 5/1998 | Luskin |
| 5,753,506 A | 5/1998 | Johe |
| 5,770,414 A | 6/1998 | Gage et al. |
| 5,824,489 A | 10/1998 | Anderson et al. |
| 5,849,553 A | 12/1998 | Anderson et al. |
| 5,851,832 A | 12/1998 | Weiss et al. |
| 5,928,947 A | 7/1999 | Anderson et al. |
| 6,497,872 B1 | 12/2002 | Weiss et al. |

FOREIGN PATENT DOCUMENTS

| | | |
|---|---|---|
| WO | WO 94/02593 | 2/1994 |
| WO | WO 94/10292 | 5/1994 |
| WO | WO 95/13364 | 5/1995 |
| WO | WO 96/09543 | 3/1996 |
| WO | WO 96/15226 | 5/1996 |
| WO | WO 98/48001 | 10/1998 |
| WO | WO 99/01159 | 1/1999 |
| WO | WO 99/11758 | 3/1999 |

OTHER PUBLICATIONS

Evans Science 240: 889-895 (1988).*
Bartlett et al. (1988) PNAS 85, 3255-3259.
Bernard et al. (1989) J. Neurosci. Res. 24, 9-20.
Brustle et al. (1999) Science 285, 754.-756.
Carpenter et al. (1999) Exp. Neurol. 158, 265. -278.
Eilers et al. (1989) Nature 340, 66-68.
Flax et al. (1998) Nature Biotech. 16, 1033-1039.
Hoshimaru et al. (1996) PNAS 93, 1518-1523.
Jung et al. (1998) Eur. J. Neurosci 10, 3246-3256.
Kilpatrick et al. (1993) Neuron 10, 255-265.
Lee et al. (1999) Oncogene 18, 2997-3003.
Nakafuku et al. (1995) J. Neurosci. Res. 41, 153-168.
Pollerberg et al. (1995) J. Neurosci. Res. 41, 427-442.
Rao et al. (1997) J. Neurobiol. 32, 722-746.
Reichmann et al. (1992) Cell 71, 1103-1116.
Renoncourt et al. (1998) Mechanisms of Development 78, 185-197.
Righi et al. (1995) J. Neurochem. 64, 121-129.
Ryder et al. (1990) J. Neurobiol. 21, 356-375.
Sah et al. (1997) Nature Biotech. 15, 574-580.
Selvakumaran et al. (1993) Blood 81, 2257-2262.
Svendsen et al. (1998) J. Neurosci. Methods 85, 141-152.
Vescovi et al. (1999) Exp. Neurol. 156, 71-83.
Wang et al. (1994) PNAS 91, 8180-8184.
Xu et al. (1996) PNAS 93, 12195-12199.
Yamada et al. (1999) Neurosci. Letters 264, 165-167.
Green et al., Nature 320: 134-139(1986).
Kumar et al., The EMBO Journal 5: 2231-2236(1986).
Stone et al., Molecular and Cellular Biology 7: 1697-1709(1987).
Watt et al., Nature 303: 725-728(1983).
Ahmed, S., Reynolds, B.A., and Weiss, S., J., Neurosci. 15, 5765-5778 (1995).
Baetge, E.E., Ann. N.Y. Acad. Sci. 695, 285 (1993).
Bartlett, P.F. et al., Clin. Exp. Pharm. Physiol. 22, 559-562 (1995).
Brustle, O. and McKay, R.D.G., Curr. Opin. Neurobiol. 6, 688-695 (1996).
Davis, A.A. & Temple, S., Nature 372, 263-266 (1994).
Feldman, D.H., Thinschmidt, J.S., Peel, A.L., Papke, R.L., and Reier, P.J., Exp. Neurology 140, 206-217 (1996).

(Continued)

*Primary Examiner*—Robert C Hayes
(74) *Attorney, Agent, or Firm*—K&L Gates LLP

(57) ABSTRACT

A systematic and efficient method for establishing stable neural stem cell lines and neuronal progenitor lines is described. The resulting cell lines provide robust, simple, and reproducible cultures of human and other mammalian neurons in commercially useful mass quantities while maintaining normal karyotypes and normal neuronal phenotypes.

19 Claims, 11 Drawing Sheets

OTHER PUBLICATIONS

Finley, M.F.A., Kulkarni, N., and Huettner, J.E., J. Neurosci. 16, 1056-1065 (1996).
Gage, F.H., Coates, P.W., Palmer, T.D., Kuhn, H.G., Fisher, L.J., Suhonen, J.O., Peterson, D.A., Suhr, S.T. & Ray, J., Proc. Natl. Acad. Sci. USA 92, 11879-11883 (1995).
Gage, F.H., Ray, J. & Fisher, L.J., Annu. Rev. Neurosci. 18, 159-192 (1995).
Gritti, A., et al., J. Neurosci. 16, 1091-1100 (1996).
Hermanson, M., Olsson, T., Wetermark, B. & Funa K., Exp. Brain Res. 102, 415-422 (1995).
Johe, K.K., Hazel, T.G., Muller, T., Dugich-Djordevic, M.M., and McKay, R.D.G., Genes Dev. 10, 3129-3140 (1996).
Kilpatrick, T.J. and Bartlett, P.F., J. Neurosci. 15, 3653-3661 (1995).
Kilpatrick, T.J., Richards, L.J., and Bartlett, P.F., Mol. Cell. Neurosci. 6, 2-15 (1995).
Littlewood, T.D., et al., "A modified oestrogen receoptor ligan-binding domain as an improved switch for the regulation of heterologous proteins". Nucleic Acids Research. 1995, vol. 23, No. 10, pp. 1686-1690, see abstract.
Lois et al (1993) Proc. Nat'l Acad. Sci. 90: 2074-2077.
Lumsden, A. And Krumlauf, R., Science 274, 1109-1115 (1996).
McConnell, S.K., Neuron 15, 761-768 (1995).
McKay, R. Science 276, 66-71 (1997).
McKay, R., Johe, K., et al., Stem cells in the developing and adult brain, Cellular and Molecular Treatments of Neurologic Diseases, Abstract, Sep. 7-10,1995, Cambridge, Massachusetts.
Morrison, S.J., Shah, N.M., and Anderson, D.J., Cell 88, 287-298 (1997).
Nolte The Human Brain: an Introduction to Its Functional Anatomy (4th Edition) Chapter 1: Introduction to the Nervous System (pp. 1-35). (1999).
Palmer, T.D., Takahashi, J., and Gage, F.H., Mol. Cell. Neurosci. 8, 389-404 (1997).
Qian, X., Davis, A.A., Goderie, S,K., and Temple, S., Neuron 18, 81-93 (1997).
Rakic, P., Proc. Natl. Acad. Sci. USA 92, 11323-11327 (1995).
Ray, J., and Gage, F.H., J. Neurosci. 14, 3548-3564 (1994).
Ray, J., Peterson, D., Schinstine, M. & Gage, F., Proc. Natl. Acad. Sci. USA 90, 3602-3606 (1993).
Reynolds, B., Tetzlaff, W. & Weiss, S., J. Neurosci. 12, 4565-4574 (1992).
Reynolds, B.A. and Weiss, S., Dev. Biol. 175, 1-13 (1996).
Sabate, O., Horellou, P., Vigne, E., Colin, P., Perricaudet, M., Buc-Caron, M.-H. & Mallet, J., Nature Genetics 9, 256-260 (1995).
Schinstine, M. and Iacovitti, L., Exp. Neurol. 141, 67-78 (1996).
Schlaggar, B.L. and O'Leary, D.D.M., Science 252, 1556-1560 (1991).
Sigma Aldrich MSDS and Information on EDTA and EGTA (downloaded from website on Jan. 21, 2005).
Stemple, D.L. and Mahanthappa, N.K., Neuron 18, 1-4 (1997).
Svendsen, C.N. & Rosser, A.E., Trends in Neuroscience 18, 465-466 (1995).
Svendsen, C.N., Clarke, D.J., Rosser, A.E., and Dunnett, S.B., Exp. Neurol. 137, 376-388 (1996).
Svendsen, C.N., Fawcett, J.W., Bentlage, C. & Dunnett, S.B., Exp. Brain Res. 102, 407-414 (1995).
Takeichi & Okada (1972) "Roles of Magnesium and Calcium Ions in Cell-to-Substrate Adhesion." Experimental Cell Research 74(1): 51-60.
Temple and Qian, Curr. Opin. Neurobiol. 6, 11-17 (1996).
Vescovi, A.L., Reynolds, B.A., Fraser, D.D., and Weiss, S., Neuron 11, 951-966 (1993).
Vicario-Abejon. C., Johe, K., Hazel, T., Collazo, D. & McKay, R., Neuron 15, 105-114 (1995).
Von Visger et al. (Jul. 1994) "Differentiation and maturation of astrocytes derived from neuroepithelial progenitor cells in culture." Exp Neurol. 128(1): 34-40.
Weiss, S., Dunne, C., Hewson, J., Wohl, C., Wheatley, M., Peterson, A.C., and Reynolds, B.A., J. Neurosci. 16, 7599-7609 (1966).
Weiss, S., Reynolds, B.A., Vescovi, A.L., Morshead, C., Craig, C.G., van der Kooy, D., Trends Neurosci. 19, 387-393 (1996).
Bartlett et al., Immortalization of mouse neural precursor cells by the c-myc oncogene, Proc. Natl. Acad. Sci. USA vol. 85, pp. 3255-3259, May 1998 Neurobiology, duplicate citation w/ Jan. 14, 2002 IDS.
Bernard et al., Role of c-myc and the N-myc Proto-Oncogenes in the Immortalization of Neural Precursors, Journal of Neuroscience Research, pp. 9-20 (1989), duplicate citation w/ Jan. 14, 2002 IDS.
Bredesen et al., Neural Transplantation Using Temperature-sensitive Immortalized Neural Cells: A Preliminary Report, Ann. Neurol, pp. 205-207 (1990).
Conover et al., Ciliary Neurotrophic Factor Maintains the Pluripotentiality of Embryonic Stem Cells, Development 119, pp. 559-565 (1993).
Escary et al., Leukaemia Inhibitory Factor is Necessary for Maintenance of Haematopoietic Stem Cells and Thymocyte Stimulation, Nature, vol. 363, pp. 361-364 (May 27, 1993).
Evrard et al., Immortalization of bipotential and plastic glio-neuronal precursor cells, Proc. Natl. Acad. Sci. USA vol. 98, pp. 3062-3066, Apr. 1990 Developmental Biology.
Guentert-Lauber, et al., Responsiveness of Astrocytes in Serum-Free Aggregate Cultures to Epidermal Growth Factor: Dependence on the Cell and the Epidermal Growth Factor Concentration, Dev. Neurosci. 7: pp. 286-295 (1985).
Hollenberg et al., Epidermal Growth Factor: Receptors in Human Fibroblasts and Modulation of Action by Cholera Toxin, Proc. Natl. Acad. Sci. USA vol. 70, No. 10, pp. 2964-2968 (1973).
Monnet-Tschudi et al., Influence of Epidermal Growth Factor on the Maturation of Fetal Rat Brain Cells in Aggregate Culture, Dev. Neurosci. 11: pp. 30-40 (1989).
Murphy et al., Fibroblast Growth Factor Stimulates the Proliferation and Differentiation of Neural Precursor Cells in Vitro, Journal of Neuroscience Research 25: pp. 463-475 (1990).
Pulliam et al., A Normal Human Brain Cell Aggregate Model for Neurobiological Studies, Journal of Neuroscience Research 21: pp. 521-530 (1988).
Resnick et al., Long-term Proliferation of Mouse Primordial Germ Cells in Culture, Nature, vol. 359, pp. 550-551 (Oct. 8, 1992).
Rudland et al., Growth Control in Cultured Mouse Fibroblasts: Induction of the Pleiotypic and Mitogenic Responses by a Purified Growth Factor, Proc. Natl. Acad. Sci. USA vol. 71, No. 7, pp. 2600-2604 (1974).
Weiss, et al.; Reexamination Control No. 90/008366 for Patent No. 7,101,709, Methods of Screening Biological Agents.
Weiss, et al.; Reexamination Control No. 90/008366 for Patent No. 7,101,709, Methods of Screening Biological Agents; Office Action in Ex Parte Reexamination.
Weiss, et al.; Reexamination Control No. 90/008367 for Patent No. 6,294,346, Use of Multipotent Neural Stem Cells and Their Progeny for the Screening of Drugs and Other Biological Agents.
Weiss, et al.; Reexamination Control No. 90/008367 for Patent No. 6,294,346, Use of Multipotent Neural Stem Cells and Their Progeny for the Screening of Drugs and Other Biological Agents; Office Action in Ex Parte Reexamination.
Carpenter; Reexamination Control No. 90/008862 for Patent No. 6,103,530, Cultures of Human CNS Neural Stem Cells.
Weiss, et al.; Reexamination Control No. 90/008580 for Patent No. 5,851,832, in Vitro Growth and Proliferation of Multipotent Neural Stem Cells and Their Progeny.
Weiss, et al.; Reexamination Control No. 90/008580 for Patent No. 5,851,832, In Vitro Growth and Proliferation of Multipotent Neural Stem Cells and Their Progeny; Office Actions in Ex Parte Reexamination.
Weiss, et al.; Reexamination Control No. 90/008581 for Patent No. 6,497,872, Neural Transplantation Using Proliferated Multipotent Neural Stem Calls and Their Progeny.
Weiss, et al.; Reexamination Control No. 90/008581 for Patent No. 6,497,872, Neural Transplantation Using Proliferated Multipotent Neural Stem Calls and Their Progeny: Office Action in Ex Parte Reexamination.

* cited by examiner

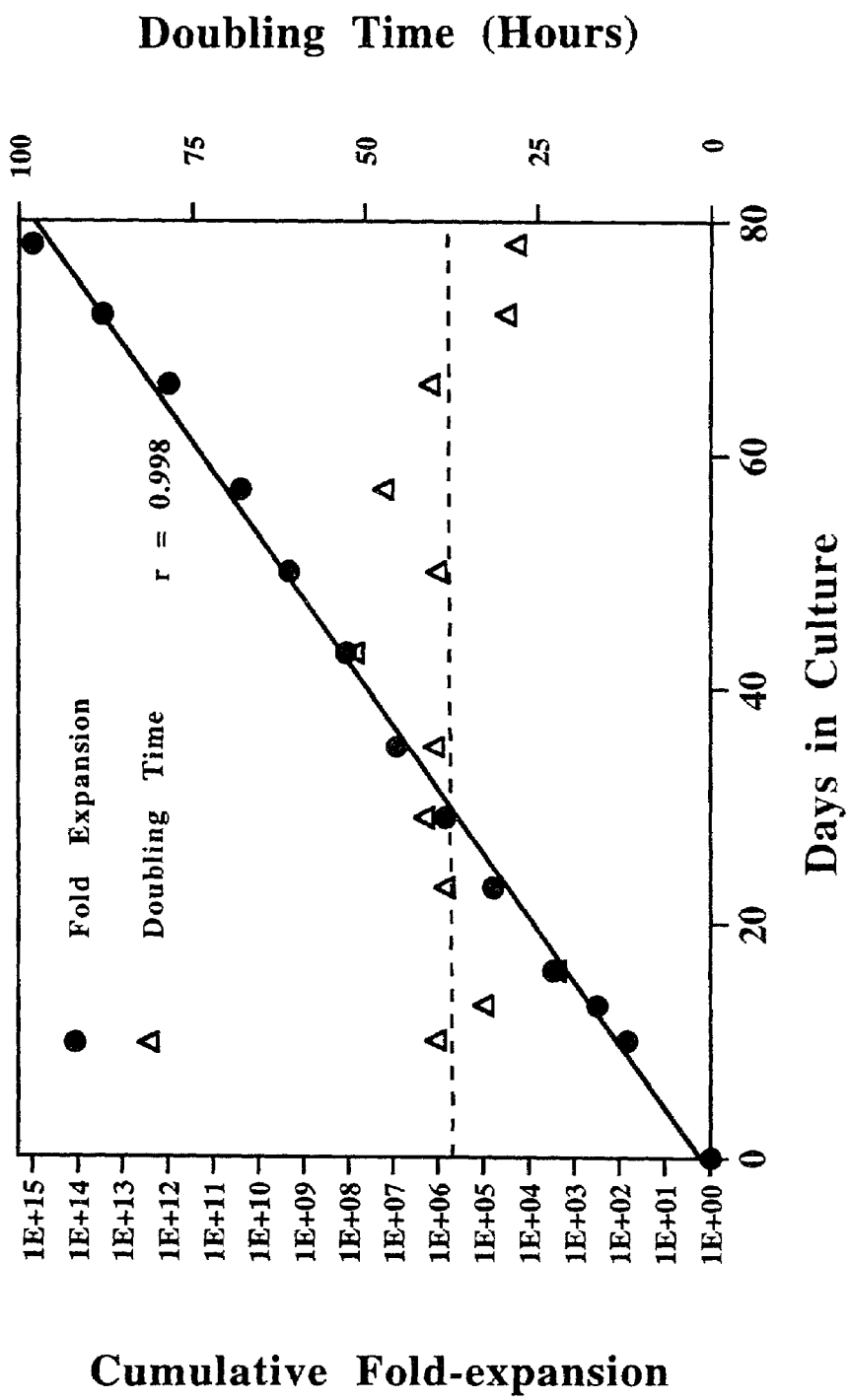

FIG. 3A
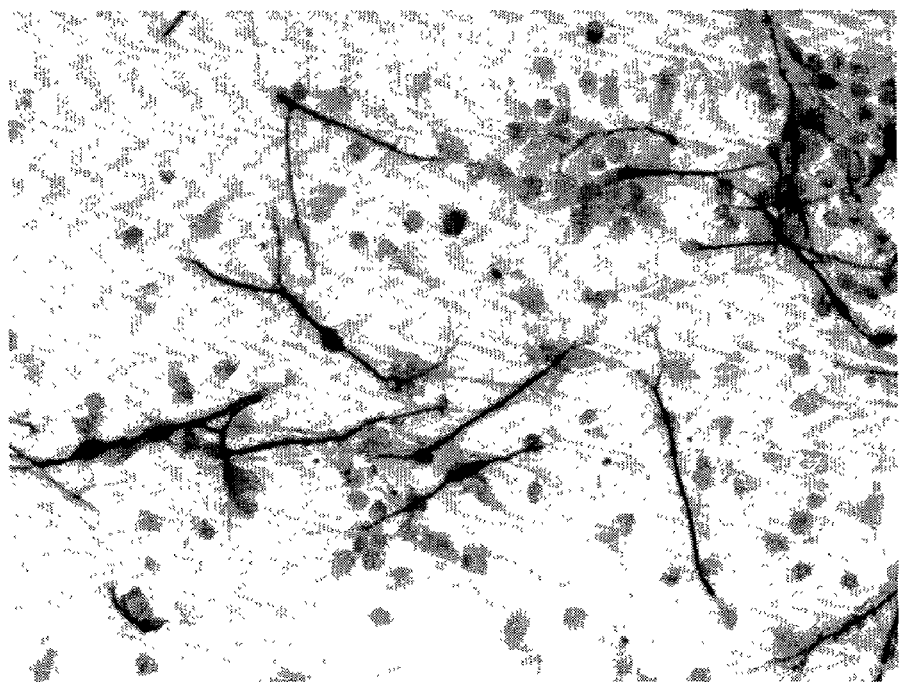
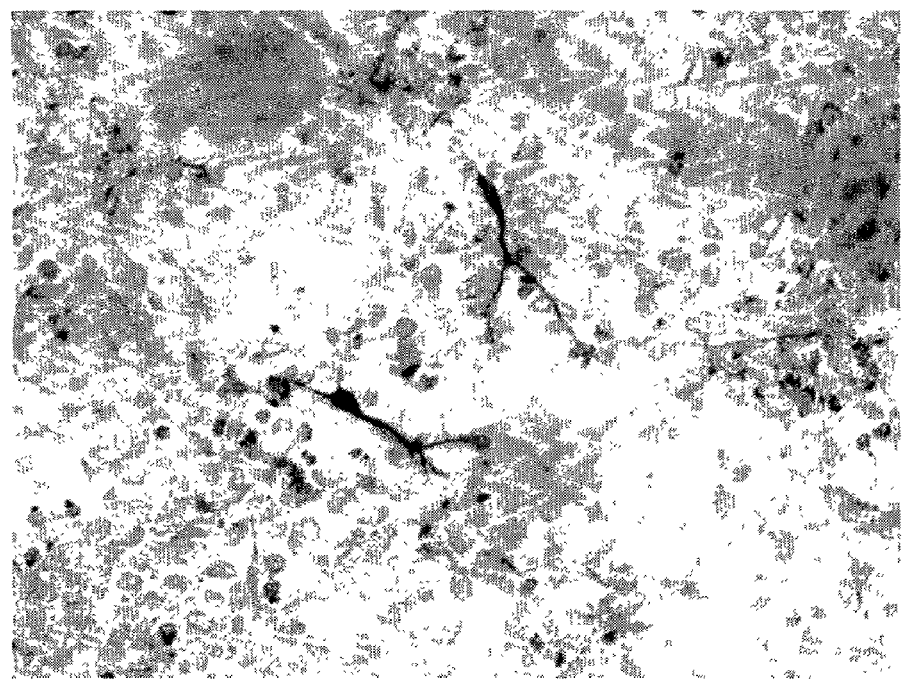
FIG. 3B

FIG. 3C
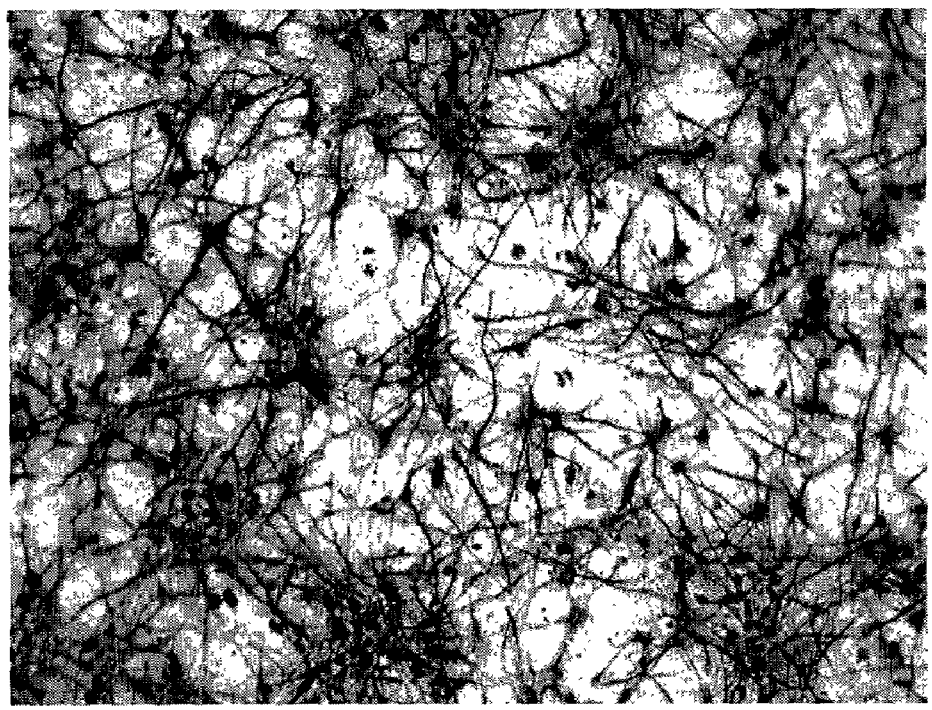
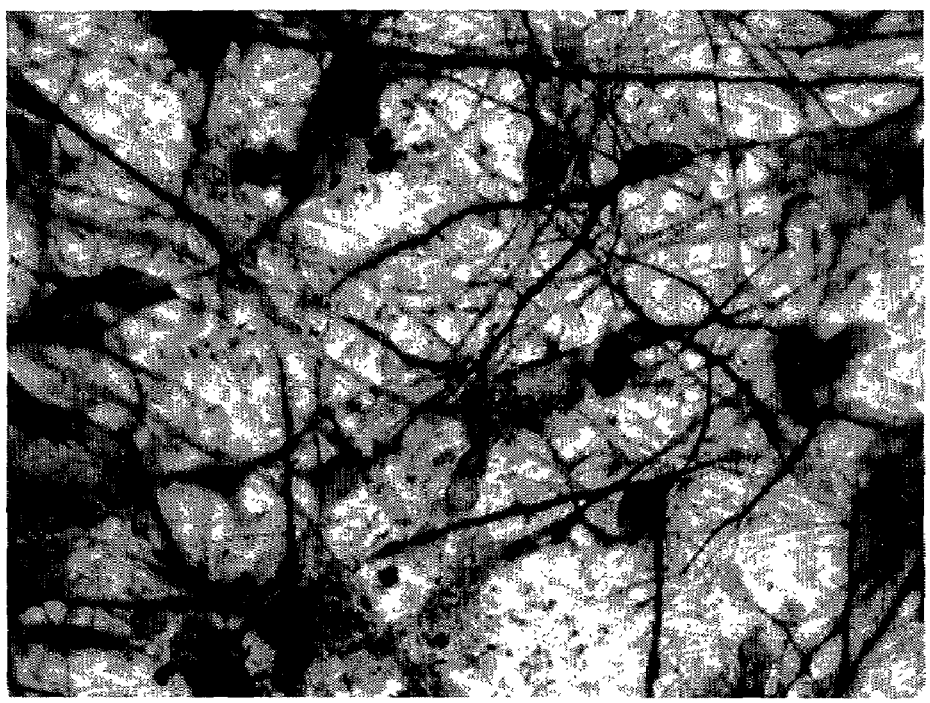
FIG. 3D

FIG. 3E
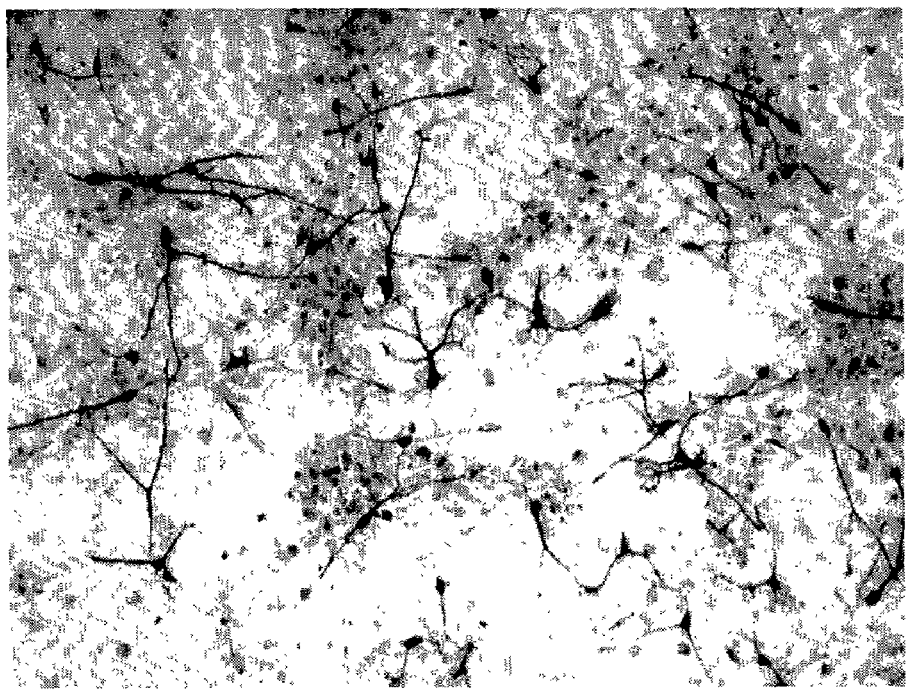
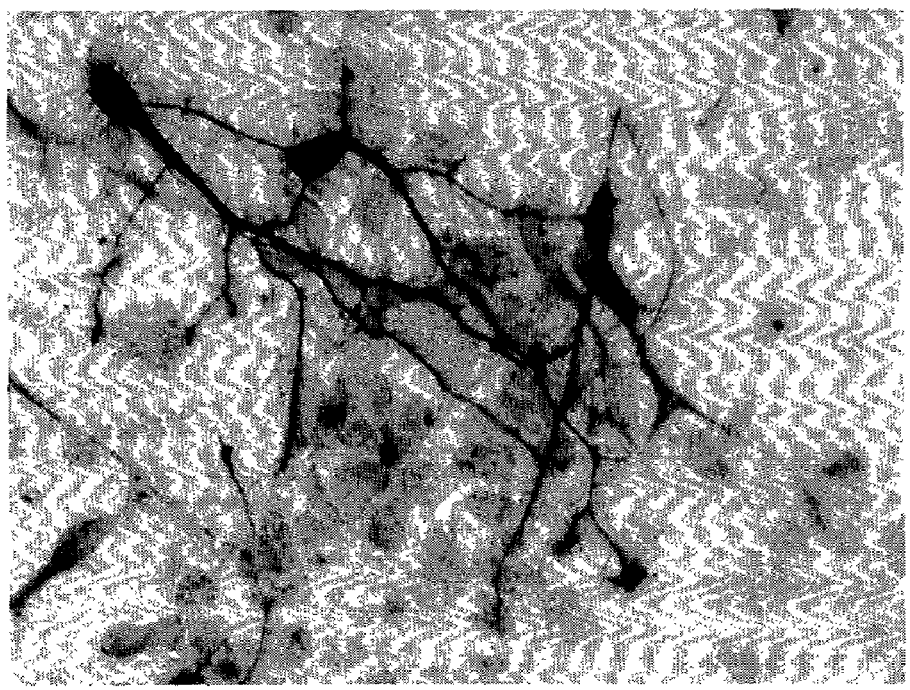
FIG. 3F

FIG. 3G
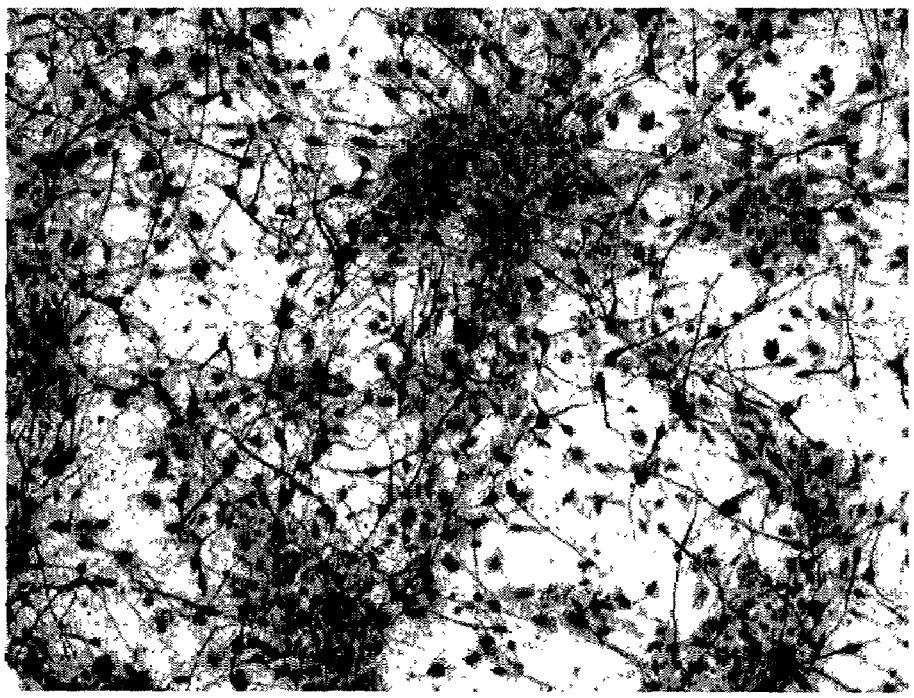
FIG. 3H

FIG. 3I
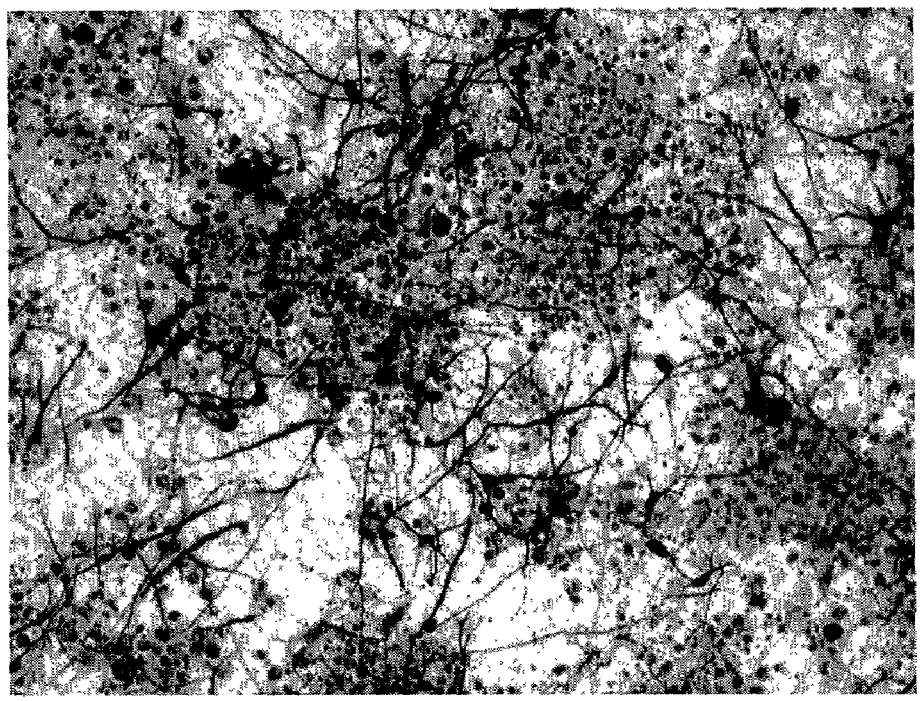
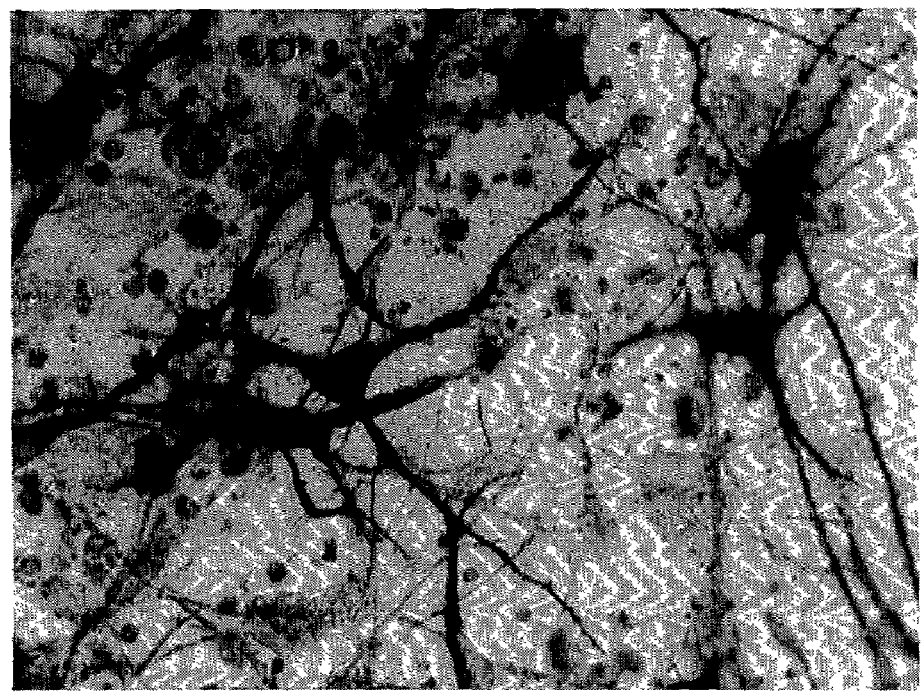
FIG. 3J

FIG. 3K
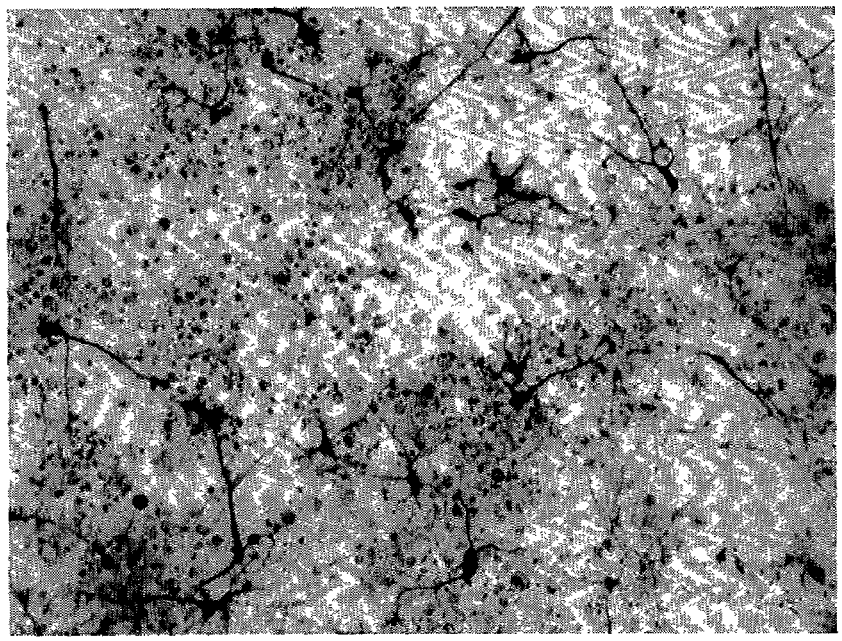
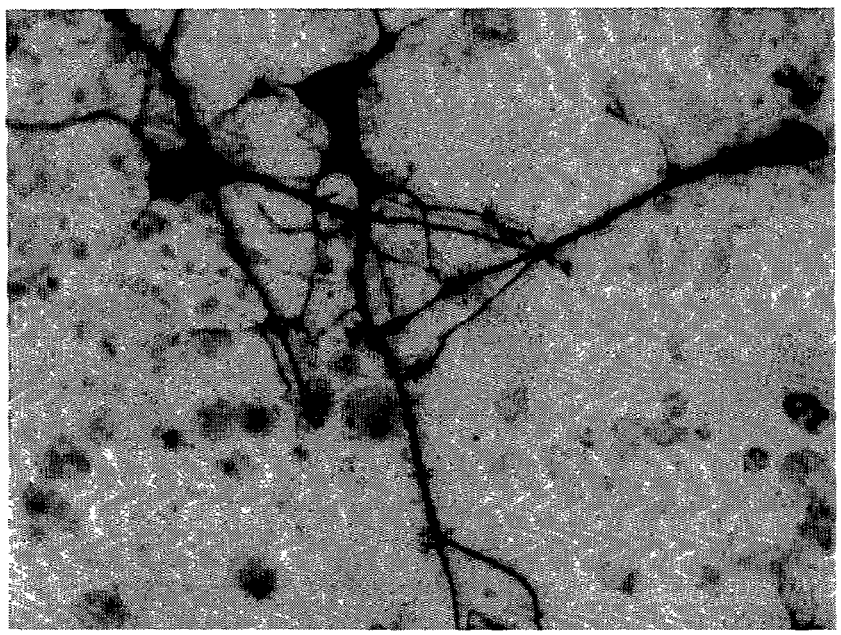
FIG. 3L

FIG. 5A
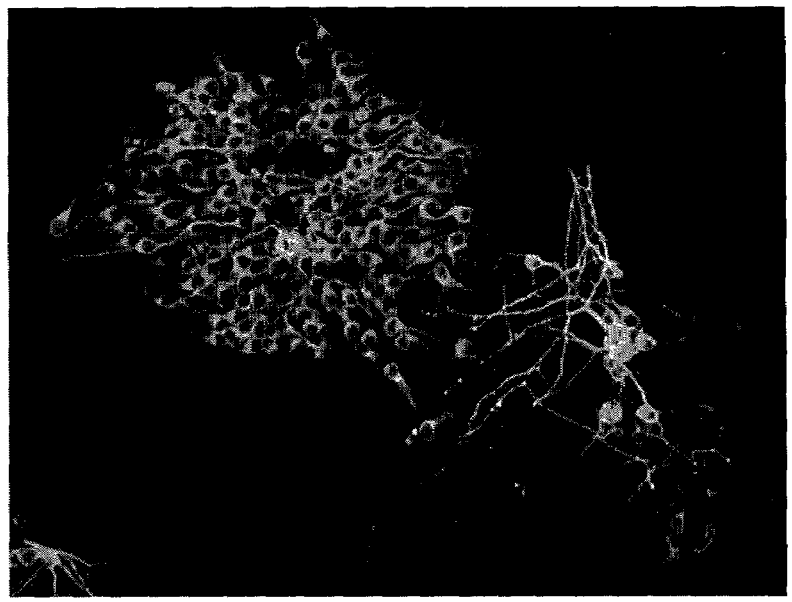
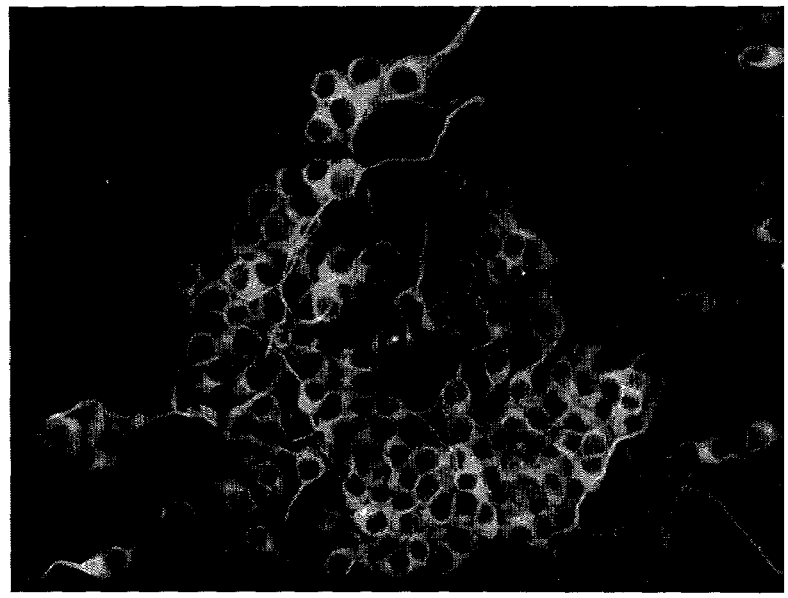
FIG. 5B

FIG. 5C
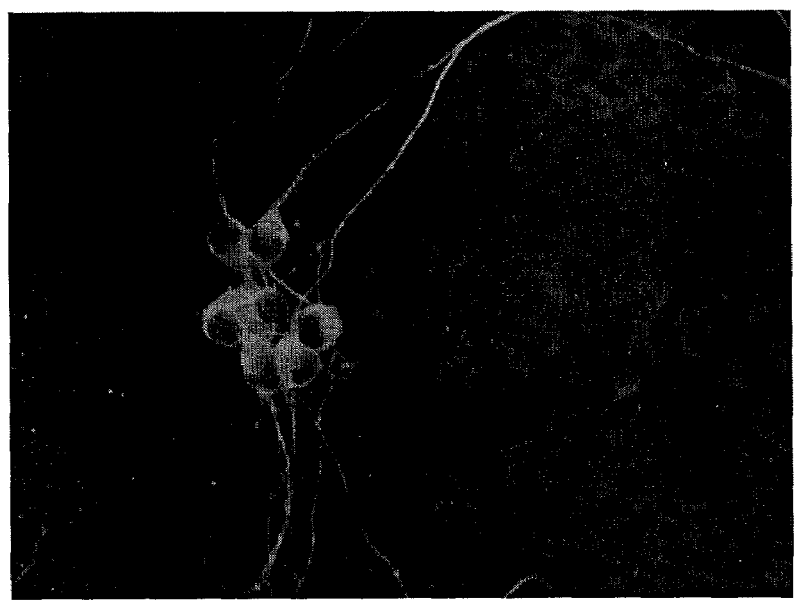
FIG. 5D

STABLE NEURAL STEM CELL LINE METHODS

This patent application is a continuation of and claims priority to and the benefit of U.S. patent application Ser. No. 09/398,897, filed Sep. 20, 1999, now abandoned, which claims priority to and the benefit of U.S. provisional patent application 60/101,354, filed Sep. 22, 1998, and is a continuation-in-part of and claims priority to and the benefit of U.S. patent application Ser. No. 09/053,414, filed Apr. 1, 1998, now abandoned, which is a continuation-in-part of and claims priority to and the benefit of U.S. patent application Ser. No. 08/719,450, filed Sep. 25, 1996, now U.S. Pat. No. 5,753,506, the entire contents of each is hereby incorporated by reference and relied upon.

BACKGROUND OF THE INVENTION

1. Field of the Invention

The present application discloses a systematic and efficient method for establishing stable neural stem cell lines and neuronal progenitor lines. The resulting cell lines provide robust, simple, and reproducible cultures of human and other mammalian neurons in commercially useful mass quantities while maintaining normal karyotypes and normal neuronal phenotypes.

2. Description of the Related Art

A developing fetal brain contains all of the cells germinal to the cells of an adult brain as well as all of the programs necessary to orchestrate them toward the final network of neurons. At early stages of development, the nervous system is populated by germinal cells from which all other cells, mainly neurons, astrocytes and oligodendrocytes, derive during subsequent stages of development. Clearly such germinal cells that are precursors of the normal brain development would be ideal for all gene-based and cell-based therapies if these germinal cells could be isolated, propagated and differentiated into mature cell types.

The usefulness of the isolated primary cells for both basic research and for therapeutic application depends upon the extent to which the isolated cells resemble those in the brain. Just how many different kinds of neural precursor cells there are in the developing brain is unknown. However, several distinct cell types may exist:

a unipotential precursor to neurons only ("committed neuronal progenitor" or "neuroblast"), a unipotential precursor to oligodendrocytes only ("oligodendroblast"), a unipotential precursor to astrocytes only ("astroblast"), a bipotential precursor that can become either neurons or oligodendrocytes, neurons or astrocytes, and oligodendrocytes or astrocytes, and a multipotential precursor that maintains the capacity to differentiate into any one of the three cell types.

CNS stem cells are multipotential precursor cells with the innate property to differentiate into all major cell types of the mammalian central nervous system (CNS) including neurons, astrocytes, and oligodendrocytes. The methods for isolation and differentiation of CNS stem cells and the characterization of differentiated cell types have been previously described in detail, U.S. Pat. No. 5,753,506 (Johe). Briefly, CNS stem cells are expanded in serum-free, chemically defined medium containing basic fibroblast growth factor, bFGF, as the sole mitogen. The culture condition permits nearly pure populations of CNS stem cells for a long period both as a mass culture and as a clonal culture.

The mitotic capacity of CNS stem cells, however, is finite. With the previous culture conditions, it had been difficult to expand CNS stem cells beyond about 30 cell-doublings at which point a majority of the cells have lost their capacity for neuronal differentiation and further expand as glial progenitors rather than as multipotential stem cells. The mechanism for this limitation is yet unknown.

We hypothesized that mitotic CNS stem cells secrete an autocrine factor or factors which suppress the entry into cell cycle at the G1 phase of mitosis. This would effectively antagonize the mitogenic actions of bFGF and initiate the differentiation path. Thus, it is a mechanism to self-regulate the proliferation of CNS stem cells and, in vivo, to limit the generation of neurons and glia during development. Consistent with this mechanism is the observation that high cell density promptly differentiates CNS stem cells even in the presence of bFGF and regardless of the passage time.

Although the 30 cell-doublings yield $10^9$-fold expansion of cells, a method for further significant expansion of CNS stem cells would be of significant commercial value. Here, we disclose that constitutive activation of c-myc protein in CNS stem cells prevents their spontaneous differentiation at high cell density, confers resistance to glial differentiation, and increases the mitotic capacity over 60 cell-doublings. This procedure thus yields more than a $10^{18}$-fold expansion of CNS stem cells.

SUMMARY OF THE INVENTION

The present application reveals a method for producing stable cell lines of mammalian neural precursor cells in vitro. The method comprises the steps of preparing a culture of neural precursor cells in a serum-free medium; culturing the neural precursor cells in the presence of a first mitogen, where the first mitogen is selected from the group consisting of aFGF, bFGF, EGF, TGFα and combinations thereof; contacting the cells with an agent capable of being taken up by the cells and capable of expressing a c-myc gene; and further culturing the cells in a medium containing the first mitogen and a second mitogen, where the second mitogen is selected from the group consisting of aFGF, bFGF, EGF, TGFα, serum and combinations thereof, with the proviso that the second mitogen is other than the first mitogen.

In a preferred embodiment of the method, the c-myc gene is fused with other DNA elements, where the other DNA elements comprise at least one element selected from the group consisting of a ligand binding domain for an estrogen receptor, an androgen receptor, a progesterone receptor, a glucocorticoid receptor, a thyroid hormone receptor, a retinoid receptor, and an ecdysone receptor.

In another preferred embodiment of the method, the medium containing the first mitogen and the second mitogen further comprises a myc-activating chemical selected from the group consisting of β-estradiol, RU38486, dexamethasone, thyroid hormones, retinoids, and ecdysone.

In a more preferred embodiment of the method, the mammalian neural precursor cells are derived from a human. In another more preferred embodiment of the method, the mammalian neural precursor cells are derived from an in vitro culture of pluripotent embryonic stem cells.

The present application also reveals a cell line produced according to this method. In a preferred embodiment of the cell line, the cells maintain a multipotential capacity to differentiate into neurons, astrocytes and oligodendrocytes. In other preferred embodiments of the cell line, the cells maintain a bipotential capacity to differentiate into neurons and astrocytes or into astrocytes and oligodendrocytes.

In more preferred embodiments of the cell line, the cells maintain a unipotential capacity to differentiate into neurons or into astrocytes.

The present application also reveals a method for producing stable clonal cell lines of mammalian neural precursor cells in vitro. The method comprises the steps of preparing a culture of neural precursor cells in a serum-free medium; culturing the neural precursor cells in the presence of a first mitogen, where the first mitogen is selected from the group consisting of aFGF, bFGF, EGF, TGFα and combinations thereof; contacting the cells with an agent capable of being taken up by the cells and capable of expressing a c-myc gene and a selectable marker; further culturing the cells in a medium containing the first mitogen and a second mitogen, where the second mitogen is selected from the group consisting of aFGF, bFGF, EGF, TGFα, serum and combinations thereof, with the proviso that the second mitogen is other than the first mitogen; and collecting c-myc treated cells and co-culturing them with feeder cells free of the selectable marker and capable of supporting survival of the c-myc treated cells in a medium containing the first mitogen and the second mitogen, with the proviso that the second mitogen is other than the first mitogen.

In a preferred embodiment of this method, the c-myc gene is fused with other DNA elements, where the other DNA elements comprise at least one element selected from the group consisting of a ligand binding domain for an estrogen receptor, an androgen receptor, a progesterone receptor, a glucocorticoid receptor, a thyroid hormone receptor, a retinoid receptor, and an ecdysone receptor.

In another preferred embodiment of this method, the medium containing the first mitogen and the second mitogen further comprises a myc-activating chemical selected from the group consisting of β-estradiol, RU38486, dexamethasone, thyroid hormones, retinoids, and ecdysone.

In a more preferred embodiment of this method the mammalian neural precursor cells are derived from a human. In another more preferred embodiment of this method, the mammalian neural precursor cells are derived from an in vitro culture of pluripotent embryonic stem cells.

The present application also reveals a cell line produced by this method. In a preferred embodiment of this cell line, the cells maintain a multipotential capacity to differentiate into neurons, astrocytes and oligodendrocytes. In other preferred embodiments of this cell line, the cells maintain a bipotential capacity to differentiate into neurons and astrocytes or into astrocytes and oligodendrocytes.

In more preferred embodiments of this cell line the cells maintain a unipotential capacity to differentiate into neurons or into astrocytes.

BRIEF DESCRIPTION OF THE DRAWINGS

FIG. 2. Growth capacity of MycER-modified human CNS stem cells. In order to measure the growth rate and capacity, a MycER-modified human CNS stem cell line pool (HK18.2) derived from 18-week old human fetal cortical tissue was continuously expanded in culture for approximately 80 days. At each passage (solid circle), the cells were harvested, counted, and a fraction replated into new plates. This process was repeated for 12 passages. By dividing the increased cell number from the initial seeding density to the time of harvest by the duration of the culture per passage, an approximate doubling time was estimated (open triangle). The dotted line across the graph represents the averaged doubling time for the entire culture period. Cumulative expansion of the cells was calculated by multiplying the multiples of increased cell number at each passage and expressed as "Cumulative Fold-Expansion" over the initial cell number at day 0. The initial starting cell number at day 0 was $5.0 \times 10^6$ cells.

FIG. 3. Stability of neuronal differentiation of MycER-modified human CNS stem cells.

A. Unmodified CNS stem cells differentiated and immunostained with anti-MAP2ab antibody;

B. Unmodified CNS stem cells differentiated and immunostained with anti-TH antibody;

C. MycER modified human cortical cells at passage 4, differentiated and immunostained with anti-MAP2ab antibody viewed at low magnification;

D. MycER modified human cortical cells at passage 4, differentiated and immunostained with anti-MAP2ab antibody viewed at high magnification;

E. MycER modified human cortical cells at passage 4, differentiated and immunostained with anti-TH antibody viewed at low magnification;

F. MycER modified human cortical cells at passage 4, differentiated and immunostained with anti-TH antibody viewed at high magnification;

G. MycER modified human cortical cells at passage 4, differentiated and immunostained with anti-GABA antibody viewed at low magnification;

H. MycER modified human cortical cells at passage 4, differentiated and immunostained with anti-GABA antibody viewed at high magnification;

I. MycER modified human cortical cells at passage 9, differentiated and immunostained with anti-MAP2ab antibody viewed at low magnification;

J. MycER modified human cortical cells at passage 9, differentiated and immunostained with anti-MAP2ab antibody viewed at high magnification;

K. MycER modified human cortical cells at passage 9, differentiated and immunostained with anti-TH antibody viewed at low magnification; and L. MycER modified human cortical cells at passage 9, differentiated and immunostained with anti-TH antibody viewed at high magnification.

Figure 4:
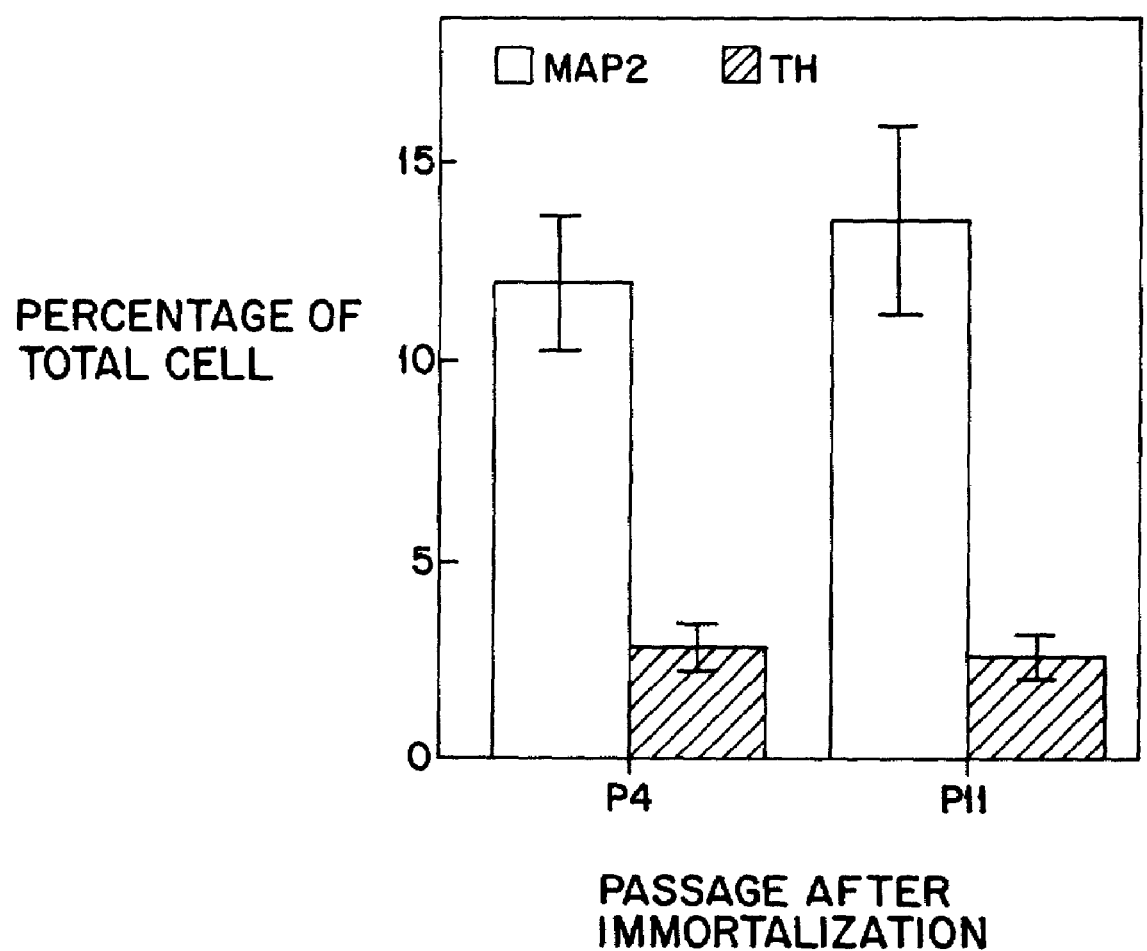

FIG. 4. Stability of neuronal differentiation. MycER-modified human cortical cell lines were differentiated at passage 4 and at passage 11. The number of neurons immunostained for MAP2ab or TH proteins were quantified and their proportions over the total cells are reported.

FIG. 5. MycER modified neuronal progenitors.

A. MycER-modified rat striatal progenitors immunostained with anti-tau antibody;

B. Morphology and arrangement of tau+/TuJ1−neuronal progenitors, immunostained with anti-tau antibody;

C. Morphology and arrangement of tau+/TuJ1+neuronal progenitors, immunostained with anti-tau antibody; and D. Morphology and arrangement of tau+/TuJ1+neuronal progenitors of C, immunostained with anti-TuJ1 antibody.

DETAILED DESCRIPTION OF THE PREFERRED EMBODIMENT

Neural cells in culture are highly plastic. Even a brief exposure to suboptimal culture conditions such as serum can have subtle yet significant long-term effects on the phenotype of the cells. Yet, almost all of the reported neural cultures employ serum as the primary source of mitogen. We and others have demonstrated that, in order to preserve the intrinsic differentiation potential of stem cells and other cells, it is critical to reduce the exposure of the cells to serum and that well-defined growth factors, particularly bFGF and/or epidermal growth factor, EGF, in a serum-free medium can proliferate a variety of different cell types in a single culture (Johe, U.S. Pat. No. 5,753,506; Weiss et. al., U.S. Pat. No. 5,851,832).

In the absence of a particular molecular marker for each of the cell types, isolating potentially thousands of distinct neural cell types that may exist in a single culture had not been feasible. In the previous works, we have described the methods and compositions of distinct CNS stem cell populations that give rise to a variety of different neurons in culture. Here, a reproducible and efficient method utilizing over-expression of the c-myc gene to stabilize the differentiation potentials of neural cells and to isolate stable clonal cell lines is described.

With continuous passage, CNS stem cells gradually lose their capacity to differentiate into neurons, thus becoming glial progenitors. The conditions which accelerate this process include high cell density during proliferation, poor attachment of the cells on extracellular matrix coated surface, and exposure to glia-promoting factors such as CNTF (ciliary neurotrophic factor), LIF (leukemia inhibitory factor), BMPs (bone morphogenic factors) and serum. In order to overcome this instability of neuronal differentiation capacity of CNS stem cells, we have introduced into the cells a cellular proto-oncogene, c-myc, whose activity can be regulated by the presence or absence of an extracellular molecule, β-estradiol.

Human and rat CNS stem cells harboring the fusion gene were grown in the continuous presence of mitogens and β-estradiol in the culture medium. Growth of the cells were significantly more robust, exhibiting faster mitotic rate, resistance to spontaneous differentiation, and much greater overall stability during the expansion. The cells showed no sign of neoplastic transformation or anomalous growth pattern or morphology. Upon withdrawal of the mitogens and β-estradiol, the cells initiated differentiation promptly and gave rise to heterogeneous morphologies characteristic of neurons and glia. Neuronal differentiation was efficient, exhibiting molecular expression patterns, localization of neurons-specific proteins, and cell morphologies and behaviors essentially indistinguishable from the parental unmodified CNS stem cells.

The neuronal population consisted of various neurotransmitter phenotypes, including the tyrosine hydroxylase-positive dopaminergic phenotype in 10-20% of the neurons. Such neuronal differentiation capacity was stable through over 60 cell doublings resulting in at least $1 \times 10^{18}$-fold increase in the number of neurons and glia derived from the stem cells. Thus, the genetic modification and the stem cell culture method described here enable the stable isolation of practically unlimited numbers of CNS stem cells from all regions of the developing mammalian brain, each CNS stem cell clone giving rise to potentially distinct neuronal subtypes in unlimited numbers. The result, then, is a library of mammalian neurons, including human, with distinct molecular/genetic repertoires representing the diverse cellular phenotypes of the mature brains.

EXAMPLES

Construction of c-Myc-estrogen Receptor Expressing Retrovirus

Figure 1:
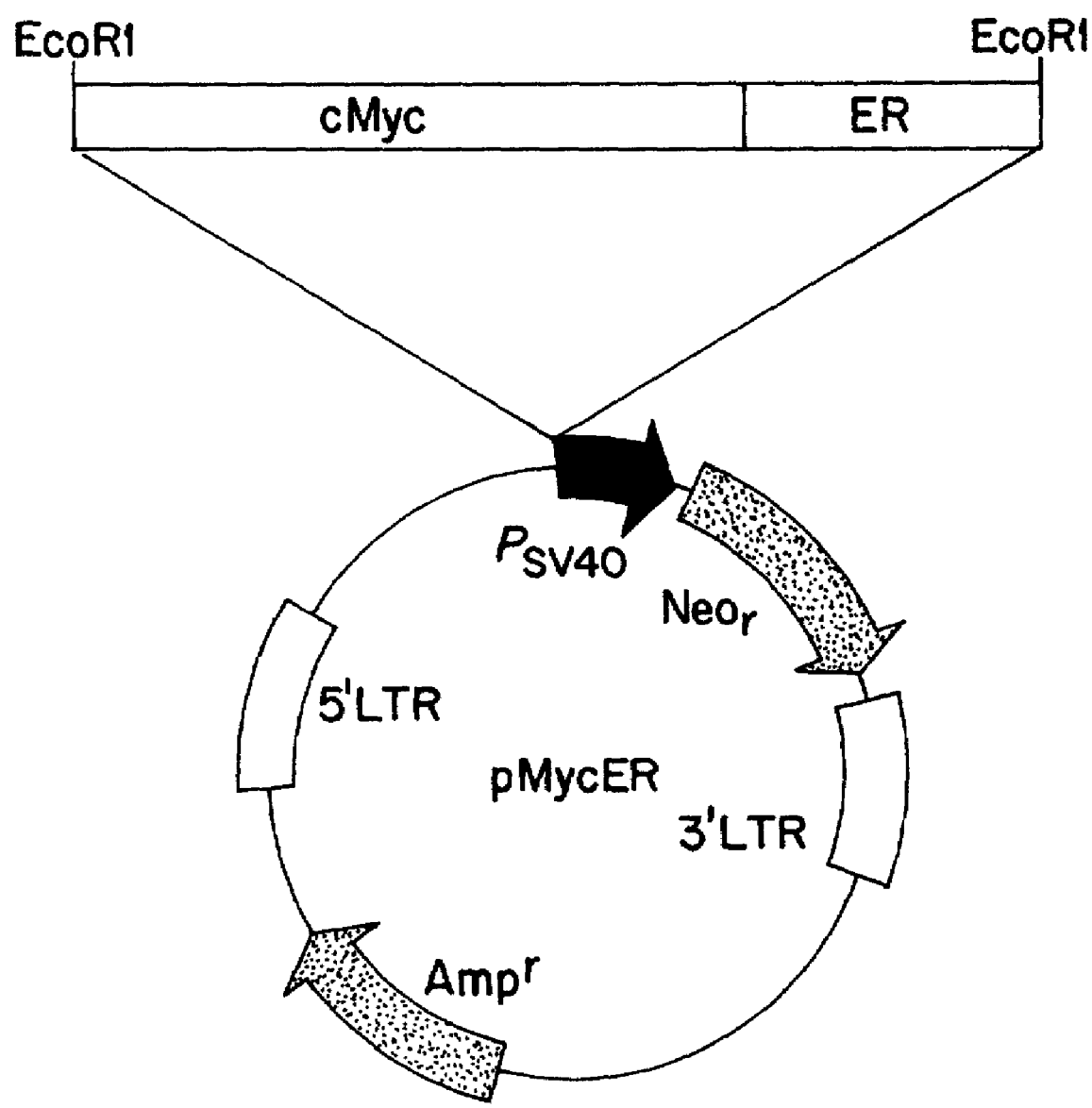
FIG. 1. Arrangement of pMycER retrovirus plasmid. A linearized EcoR1 fragment containing the human c-myc gene fused to the ligand binding domain of the human estrogen receptor gene (Eiler et al.,1989, Nature 340: 60-68) was ligated downstream of the 5'LTR of pLXSN retroviral expression plasmid (Clontech). The final construct also contains a selectable marker, the neomycin resistance gene, Neo$^r$, under the SV40 promoter, $P_{SV40}$.

A retroviral vector containing the neomycin-resistance gene under the SV40 promoter was linearized with EcoRI and ligated with the EcoRI-fragment of the DNA encoding a fusion gene of human c-myc cDNA and human estrogen receptor cDNA (Eiler et al., 1989, Nature 340: 60-68). The fusion gene was placed under the regulation of MMLV long-terminal repeat sequence (LTR). The overall arrangement of the final retroviral vector, pMycER, is shown in FIG. 1.

Generation of a Producer Cell Line

To establish a cell line stably producing the MycER retrovirus, an amphotropic packaging cell line was transfected with pMycER plasmid. Stable clones were selected with G418 (1 mg/ml, Life Technology Inc., MD) for 4 weeks. Twenty clones were screened for high titer production against Hela cells according to standard procedure. A cell line, MycER.10, with a retroviral titer of $10^5$ pfu/ml as measured by infection of rat striatal stem cells was selected for subsequent experiments.

Infection of Rat and Human CNS Stem Cells

Rat and human CNS stem cells were prepared according to previously reported procedure (U.S. Pat. No. 5,753,506). Passage 1 cells were plated at $0.5 \times 10^6$ cells per 100 mm plate and grown for three additional days in serum-free N2 medium plus 10 ng/ml bFGF. MycER.10 cells were grown in DMEM/10% fetal bovine serum to 50-75% confluence, subsequently rinsed three times with DMEM, and incubated for 4-16 hours in a retrovirus collection medium (IFM). IFM consisted of the standard N2 components (25 mg/L human recombinant insulin, 100 mg/L human apotransferrin, progesterone, putrescene, sodium selenite) in DMEM plus 10 ng/ml bFGF and 1 µg/ml human plasma fibronectin (hFN). IFM containing the retrovirus was clarified by two centrifugations at 1400 rpm and 3000 rpm. The supernatant was mixed with fresh N2 at a 1:1 ratio with fresh bFGF and hFN at 10 ng/ml and 1 µg/ml final concentrations, respectively, and applied to the 50-75% confluent CNS stem cell culture. The infection period was typically 6 hours. Human CNS stem cells were infected for 1-3 times over a 2-3 day period to compensate for their slow mitotic rate. Subsequently, the cells were rinsed three times with $Ca^{2+}$-, $Mg^{2+}$-free Hank's balanced saline solution (HBSS), passaged, and further expanded in N2 plus 10 ng/ml bFGF.

Selection of MycER-expressing CNS Stem Cells

The CNS stem cells with stable incorporation of MycER retrovirus were passaged 1-2 days after the infection, replated at $0.5 \times 10^6$ cells per 100 mm plate, and selected from 2 days after the infection with 0.1-0.2 mg/ml G418, pH 7.4. The complete, optimal growth medium (IGM) was composed of DMEM/F12 (1:1), 25 mg/L human recombinant insulin, 100 mg/L human apotransferrin, progesterone, putrescene, sodium selenite, 10 ng/ml bFGF, 0.2 µM β-estradiol, 0.1 mg/ml G418, and 10 ng/ml EGF or 1% fetal bovine serum. Fresh bFGF (10 ng/ml, final concentration) was added daily and medium was changed once every two days. The cells were passaged at approximately 50-75% confluence by rinsing three times with HBSS and trypsin (1×) treatment. Trypsin activity was stopped by adding soybean trypsin inhibitor (1 mg/ml final concentration).

Isolation of Clones

At the end of the G418 treatment for 14 days, the cells were passaged and replated approximately 200-1000 cells per 100 mm plate. Within 24 hours post plating, well-isolated single cells were marked with 3 mm circles on the bottom of the culture plate. Sometimes, the complete culture medium was mixed with an equal volume of the medium conditioned by the same cells at high cell density to enhance cell survival. Marked clones were picked with the aid of cloning rings and by trypsin treatment. Individual clones were expanded as the mass culture and stored frozen.

Almost all of the clones generated this way eventually assumed glial morphology and failed to differentiate into neurons, even though the culture conditions are identical as those for the high density culture. Thus, it became apparent that the MycER-modified cells in the presence of serum required a relatively high cell density in order to maintain their native differentiation potentials and survive. Thus, the cell density was maintained in the range of $0.5 \times 10^6$ to $1.0 \times 10^6$ cells per 100 mm plate by supplementing the clonal density of MycER-expressing cells with unmodified primary stem cells. By maintaining antibiotic selection over 5-8 days with 0.1 mg/ml G418, the feeder cell population was gradually killed while permitting local cell density of G418-resistant MycER cells to gradually rise so as to sustain their optimal growth. The antibiotic selection was maintained throughout subsequent expansion to ensure all remaining cells were MycER-modified cells.

In addition to neural stem cells, immature glial cells and mature astrocytes of both human and rat origin were effective. Fibroblasts were also useful, but more difficult to manage because their rapid proliferation rate and their high tolerance to G418. Neurons may also be useful, but their post-mitotic nature rendered them much more resistant to G418. Non-mitotic fibroblasts and other non-neural cells which had been gamma-irradiated or treated with mitotic inhibitors such as arabinoside C or mitomycin may also be effective in supporting the c-myc-modified neural cells.

Differentiation and Characterization of the Mitotically Enhanced CNS Stem Cells

CNS stem cells stably expressing MycER were differentiated by plating the cells at 100,000 cell/cm$^2$ or higher cell density and replacing the growth medium with N2 without bFGF, without serum, and without β-estradiol. Typically, the cells were allowed to differentiate for 6-30 days before immunohistochemical analysis.

Results

1. Search for Additional Factors Enhancing Mitotic Capacity of CNS Stem Cells

The doubling time for human CNS stem cells in N2 medium with bFGF as the sole mitogen is approximately 60 hours which is markedly slower than 24 hours for rat CNS stem cells under the identical culture conditions. This may be due to a species difference in certain cell-autonomous properties of the cells such as a difference in DNA replication rate or in other mitotic phases, G1 or G2, of the cell cycle. We investigated other factors to accelerate the mitotic rate of human CNS stem cells.

Many purified recombinant human growth factors were tested for the ability to enhance the mitogenic activity of bFGF. The mitotic rate of human CNS stem cells was assessed by measuring the proportion of the cells which have incorporated the mitotic label, bromodeoxyuridine (BrdU), during a 24-hour period. Each growth factor was supplied daily to the culture in addition to bFGF. Only the combination of bFGF+EGF and bFGF+TGFα (transforming growth factor-alpha) accelerated beyond the bFGF-induced mitotic rate of the human CNS stem cells. In both conditions, the doubling time of the cells increased 1.5 times to 40 hours over bFGF alone. Combination of bFGF and fetal bovine serum at 1% or at 10% also accelerated the BrdU-incorporation rate of bFGF-induced mitotic rate of CNS stem cells to a similar rate.

2. Resistance of CNS Stem Cells Against Spontaneous Differentiation

Although EGF, TGFα, 1%FBS, or 10%FBS plus bFGF increased the mitotic rate of human CNS stem cells, even under these conditions, CNS stem cells were susceptible to spontaneous differentiation at near-confluent cell density and also prone to drift toward glial progenitor states with multiple passages. In order to provide enhanced mitotic capacity and greater stability to the neuronal differentiation capacity of CNS stem cells, we constructed a retroviral vector expressing a fusion protein of human c-myc and human estrogen receptor genes under the MMLV long terminal repeat (FIG. 1).

Dividing mammalian CNS stem cells were infected by the amphotropic retrovirus with high efficiency and the resulting cells selected by their resistance to G418 treatment. The transcriptional activity of c-myc in the fusion protein (MycER) was regulated by the presence or absence of the estrogen receptor ligand, β-estradiol, in the culture medium. Moreover, the promoter activity of the long terminal repeat is shut down during CNS stem cell differentiation into neurons, effectively eliminating MycER transcript. Combination of the withdrawal of mitogens, absence of β-estradiol, and limited transcription activity of LTR resulted in an efficient constitutive differentiation of CNS stem cells in a manner indistinguishable from the unmodified parental cells.

CNS stem cells from various regions and developmental stages of human fetal brains were infected at passage1 with the MycER-expressing retrovirus. Infected cells were selected by G418 resistance and expanded in N2B medium (N2 without phenol red) containing bFGF, 10 ng/ml EGF or 1% FBS, and β-estradiol. Expression of MycER itself did not cause a significant change in the mitotic rate of the cells; however, the addition of EGF and/or FBS significantly increased the mitotic rate and enhanced the overall stability of the culture. The cells proliferated robustly, maintained stable morphologies over many successive passages, and sustained their multipotentiality without spontaneous differentiation even at nearly confluent cell density. Upon replacement of the growth medium with N2B without any mitogen and without β-estradiol, the stem cells promptly differentiated to give rise to neurons, astrocytes and oligodendrocytes.

3. Expansion Capacity of the Mitotically Enhanced CNS Stem Cell Lines

To ascertain the extent of the mitotic and differentiative capacity of the MycER-modified human CNS stem cell line, the cells were expanded continuously for 80 days in culture and through 12 passages since the infection event. During this period, the cell yield at each passage was measured to quantify the actual arithmetic increase in cell number and to determine the stability of the mitotic rate over time (FIG. 2). Overall, the cells went through approximately 54 doublings which resulted in $10^{15}$-fold increase in the cell number. The doubling time of the cells was remarkably constant at about 40 hours per mitosis, which is unchanged from that of the parental primary human CNS stem cells (FIG. 2).

The same human CNS stem cell preparation was also subjected to MycER-retrovirus infection and grown in bFGF alone or in bFGF and EGF. In bFGF alone as the mitogen, the MycER-expressing CNS stem cells exhibited enhanced mitotic capacity over the unmodified cells, but yet showed far less proliferative capacity than in bFGF+1% FBS. As with the unmodified parent cells, the MycER cells also retained a 60 hour doubling time in bFGF alone. On the other hand, in bFGF+EGF, the MycER expressing stem cells displayed increased mitotic rate, increased mitotic capacity, increased stability of neuronal differentiation capacity, and were resistant to spontaneous differentiation quite similar to the bFGF+ 1% FBS condition. In the absence of MycER expression, the same three conditions yielded a similar pattern of growth, but with less stability. Significantly, the bFGF+1%FBS condition, although resulting in more efficient cell growth, inevitably led to the loss of the neuronal differentiation capacity. This demonstrates that the constitutive c-myc function in these cells is subtle: It provides more stable multipotentiality and enhanced mitotic capacity but not an overt mitogen-independence or transformation.

These effects of the constitutively active c-myc could also be extended to CNS stem cells from all regions of rat and human fetal brains.

4. Neuronal Differentiation of MycER-enhanced CNS Stem Cells

The MycER-enhanced CNS stem cells were differentiated by withdrawing the mitogens and β-estradiol from the medium and without addition of exogenous factors. Divergence of neuronal and glial morphologies began to occur within two days. By the third day, neuronal morphologies were clearly distinguishable. The neurons continued to mature into fully functional neurons over the next 3-5 weeks.

The differentiated cultures from the MycER-enhanced human CNS stem cells at different passages were analyzed by immunohistochemistry with a variety of different cell-type specific antibodies. At 10 days of differentiation, approximately 50% of the total cells expressed MAP2c, tau, and tubulin IIIb proteins, all relatively early markers of neuronal differentiation. Approximately 20-30% of the total cells expressed the mature markers of neurons, MAP2a and MAP2b proteins. Various neurofilament antibodies revealed a similar proportion of neurons. Of the neurons, approximately 70% were GABA-positive. A similar proportion of neurons was also calretinin-positive. Approximately 10-20% of the neurons expressed tyrosine hydroxylase (TH), the key biosynthetic enzyme for dopamine. All of the immunopositive neurons were of typical neuronal morphologies and did not co-express the glial marker, GFAP. Thus, MycER-enhanced cell lines differentiate to generate a high proportion of neurons exhibiting various neurotransmitter phenotypes.

The proportions and neurotransmitter phenotypes of the neurons were stable through many successive passages (FIG. 3A-L). Throughout 54 stem cell doublings, there was no degradation of the neuronal differentiation capacity in both the proportion of neurons as well as in the various neurotransmitter phenotypes generated.

5. Region-specific Stem Cell Lines

The serum-free culture condition used for isolation of neural stem cells permitted stable inheritance of regional identities and their related neurotransmitter phenotypes through multiple cell divisions. This implies that the stem cells in the culture, although they are uniform in their ability to differentiate into neurons and glia, may be extremely diverse. Thus, if each stem cell in the beginning of the culture could be immortalized in its native state and if this method was efficient to sample thousands of stem cells in a single dish, then the diverse neuronal phenotypes might be permanently "captured" in the form of cell lines.

The genetic modification of neural stem cells with c-myc resulted in robust, highly reproducible and in a stable cell culture system. The modification process itself is quite efficient, yielding 5,000 to 50,000 independent clones per retrovirus infection over a two day process. This could be easily scaled up by increasing the retrovirus particles or increasing the number of target cell density, if needed.

In order to ascertain whether over-expression of c-myc has an impact on differentiation capacity of neurotransmitter phenotypes, stem cells from many different regions of the fetal brains of rat and human were modified by the MycER retrovirus. These regions included cortex, septum, hippocampus, midbrain, hindbrain, striatum, and spinal cord. Multiple examples of cortical, midbrain, and spinal cord cultures from several different gestational ages were examined to assess the reproducibility of the method. In all cases, the resulting pools of independent clones generated highly reproducible ratios of neurons to glia. As expected, morphologies, antigenic profiles of the neurons, and their relative ratios were also distinct from cell lines of one region versus another.

Thus, when several pools of cell lines from midbrain tissues of 8 week human fetuses were examined, approximately 0.1% of total cells were consistently TH-positive dopaminergic neurons, which is also the proportion found in the unmodified stem cell cultures. Clonal analysis revealed that the TH expression was clonally restricted. That is, a majority of the clones did not contain neurons expressing TH. Of those that did, the proportion was variable from one clone to the next. Several pools of cell lines from cortical tissues of 17-20 week old human fetuses were also examined. Interestingly, all of the cortical lines gave rise to significantly increased TH-positive neurons compared to the unmodified stem cells. The proportion of TH-positive neurons was 2-4% of the total cells. Subsequently clonal analysis revealed a similar pattern in the distribution of the TH-positive neurons. The majority had none, while those that generate TH were present in variable proportions. This pattern had also been observed with clones of unmodified stem cells from several different regions and with several different antigenic markers.

Cell lines from spinal cord of 6-10 week old human fetuses were also established. The pattern of neuronal differentiation was the same as from other regions, although their stem cell morphology and growth characteristics were distinct.

Thus, the genetic modification of neural stem cells with c-myc does not alter their intrinsic differentiation capacities. In all of the cell lines through extensive continues culture periods, no evidence of tumor formation or other abnormal transformation was noted. Upon karyotype analysis of one pool of human cortical cell lines at passage 14, a normal diploid chromosome pattern with no aberrant rearrangement was observed. Thus, regulation of mitotic capacity by c-myc, which is a cellular gene normally present in every eukaryotic cell and a well-known key regulator of cell cycle machinery, is not oncogenic and provides significant advantages over other methods using viral oncogenes such as v-myc or SV40 large T antigen.

6. Other Cell Types

The genetic modification with c-myc can be made at any time during the culture period. Since the expression of c-myc itself is not mitogenic, i.e., non-transforming, a culture condition which promotes the proliferation of a particular neural precursor population is a prerequisite. Purified growth factors such as aFGF (acidic fibroblast growth factor), bFGF, EFG and TGFα can proliferate a variety of different neural cell types. Although most of the descriptions above were on multipotent CNS stem cells as one predominant population, several different cell types were observed during clonal analysis.

One significant population was a population of bipotential progenitor clones which, upon differentiation, gave rise to neurons and astrocytes with apparent absence of oligodendrocytes. These bipotential progenitors were quite similar to the multipotential stem cells in their morphology during growth. The differentiation pattern was also similar giving rise to about 50% neurons and 50% astrocytes. Thus, key defining difference between the two populations is the absence of oligodendrocytes in differentiated cultures.

A second cell population arising from c-myc modification of primary neural cultures was a population of unipotential neuronal progenitor clones which consisted only of neurons. These neuronal progenitor clones were of smaller clone size and assumed distinct, immature neuronal morphologies during proliferation and expressed tau proteins and/or beta-tubulin III. Examples are provided in FIG. 5. Two distinct cell types were observed (FIG. 5A). One type was small-bodied cells with very short single process stemming out from the cell body, which grew in tight clusters. These cells were immunoreactive with anti-tau antibody but not with anti-tubulin IIIb antibody while dividing (FIG. 5B). The other type of cells were cells with distinctively elongated neurites without extensive branching, which grew in a smaller, more scattered pattern suggesting higher migratory capacity. In contrast to the first type, they were also immunoreactive with both anti-tau antibody and with anti-tubulin IIIb antibody (FIGS. 5C and 5D, respectively). Often times, the second cell types were found near or intermixed with the first cell type suggesting that they are two stages of a single continuous lineage—committed neuronal progenitors, with tau+/TuJ1+ state being the more mature state.

A third cell population arising from c-myc-modified neural cell culture was a population of clones consisting of glia only. Most of these clones were astrocytic with little or no oligodendrocytes.

These results indicate that many neural precursor lineages respond similarly to the over-expression of c-myc. In addition to primary neural cultures prepared from nervous system tissues of mammals, recent advances in embryonic stem cell cultures indicate that various neural precursors form in vitro during differentiation of totipotential or pluripotent embryonic stem cells and cell lines maintained in culture for long term (Renoncourt et al., Mech. Dev. (1998) 78, 185; Svendsen et. al., Trends Neurosci. (1999) 22, 357; Brustle et. al., Science (1999) 285, 754.). These cultures can generate nestin-positive neural precursor cells which can then be transferred to serum-free medium and subsequently expanded with bFGF and/or EGF for short term. Long-term, mass expansion has not been feasible since the initial neural precursor formation is inefficient. However, by utilizing the genetic modification method with c-myc gene described here, those transient neural precursors may be turned into stable cell lines.

Neural precursors including multipotential neural stem cells can be isolated from adult brains and can be cultured in serum-free conditions. However, this process is inefficient, resulting in only a small number of proliferative cells. However, with the transfer of c-myc gene as described here, one can establish stable cell lines from such small number of cells obtained from neural tissue biopsies.

c-myc is involved in many different cellular processes such as apoptosis in addition to cell cycle regulation. c-myc has been used previously to transform cells of non-neural origins. However, these previous studies were done with already stable cell lines such as 3T3 fibroblast cell lines and to produce neoplastic state of the cell lines, which had been selected based on spontaneous chromosomal aberrations which conferred mitogen-independence. Other studies tried to use an immortalization process to turn post-mitotic neurons to re-enter the cell cycle.

CNS stem cells are already mitotic and the mitogenic culture conditions for a long-term expansion of up to 30 cell doublings has already been established. Thus, our objective has been to increase the expansion capacity well beyond the 30 cell doublings at least up to the beginning of senescence which is thought to occur between 60 and 80 cell cycles. Sixty cell doublings represent an $1 \times 10^{18}$-fold increase in cell number which is large enough for screening one million chemical libraries, each consisting of 500,000 compounds or large enough to provide cell therapies for 50 billion Parkinson's patients. The key concept has been to find a "gentle" modification of the cells so as not to disrupt their intrinsic neuronal differentiation capacity while providing an enhanced growth capacity under the culture conditions established for primary CNS stem cells.

Increasing the concentration of active c-myc protein leads to the generation of stable human CNS stem cell lines. This effect occurs not by overtly deregulating mitotic and differentiation parameters of the cell cycle but by providing resistance to autocrine and paracrine factors that induce restriction of multipotentiality toward a glial progenitor state. The consequence is not an oncogenic transformation of the cells but rather a stabilization of the cell growth. Thus, endogenous signals which trigger the differentiation, such as those present at confluent cell density, are still effective. The cell division is still dependent upon the supply of proper exogenous mitogens such as bFGF and/or EGF and/or serum. Differentiation of the stem cell lines to mature functional neurons is as efficient at the end of the 60-cell doublings as in the unmodified primary cells. A variety of neurotransmitter phenotypes and their relative proportions are maintained throughout the expansion.

The c-myc activity in these examples was controlled by constructing a chimeric protein of c-myc fused to a fragment of estrogen receptor protein (Eiler et. al., Nature (1988) 340, 60). The intended role of the estrogen is to provide a control over the amount of functionally active c-myc induced in the cell. The estrogen receptor portion of the chimeric protein is activated when it binds with a cell-permeable agonist or antagonist such as β-estradiol or tamoxifen.

Most members of the nuclear receptor superfamily act similarly in that cell-permeable ligands diffuse through the plasma bilayer and bind to their receptor which is then transported to the nucleus as a complex and induces a variety of transcription related events. The ligand binding domain of these nuclear receptor proteins and their ligands can substitute for the estrogen receptor and β-estradiol in order to regulate functions of the fused c-myc protein moiety. Examples of such nuclear receptors are glucocorticoid receptor, progesterone receptor, androgen receptors, vitamin D receptor, thyroid hormone receptors, retinoic acid receptors, and ecdysone receptor. Each of these receptors can be activated intracellularly by adding to the culture medium its appropriate ligands. Examples of the ligands are steroid hormones such as glucocorticoid or dexamethasone, thyroid hormones, retinoids such as retinoic acids, vitamin D, and the insect molting hormone, ecdysone, as well as their synthetic analogs designed to act on the respective receptors. All of these compounds are small, hydrophobic molecules which can traverse the cell membrane once supplied extracellularly.

Some receptor-ligand systems are better suited than others for the purpose of regulating the over-expressed c-myc. For instance, for the purpose of transplanting c-myc-modified cells into tissues as a treatment of a disease, it would be desirable that the c-myc-receptor chimeric protein should not respond to endogenous physiological ligands. The c-myc-estrogen receptor described here has the disadvantage that potentially high level of estrogen present in female patients may have unexpected effects on the cells. In another instance, the ligands used to control the c-myc activity in culture may have their own unrelated effects on endogenous receptors. Thus, an ideal receptor-ligand system is one in which the receptor moiety of the fusion protein does not recognize the endogenous ligand and in which the ligand is a synthetic compound which has no adverse effect on the cells. One such potential system is human progesterone receptor and its antagonist ligand, RU38486. It has been established that the ligand binding fragment of the human progesterone receptor does not respond to the endogenous ligand, progesterone but is sensitively activated by a synthetic analog of progesterone, RU38486, while RU38486 does not activate the endogenous full-length progesterone receptor (Wang et al., Proc. Natl. Acad. Sci. USA (1994) 91, 8180).

Thus, one enhanced c-myc expression system to produce stable cell lines would be to construct a plasmid in which the human c-myc gene is fused to the ligand binding domain of the human progesterone receptor with the C-terminal deletion of 12 amino acids, to cut out the fused DNA (c-mycPR), ligate to the retroviral plasmid, pLXSN, at downstream of 5' LTR, and to generate the intact retrovirus expressing the chimeric protein, c-myc-progesterone receptor (MycPR).

The commercial utilities of the mitotically enhanced CNS stem cells are: cell transplantation of the TH-positive dopaminergic neurons to treat Parkinson's disease; -substrate for screening potential pharmacological compounds; a reproducible source of gene and protein levels of the cells influenced by a specific agent or protocol designed to represent/mimic a disease process; a reproducible source of novel genes and proteins; a reproducible source of neurons and glia for engineering of three dimensional tissues and neural prosthesis; a delivery vehicle of potentially therapeutic large molecule compounds such as NGF to treat Alzheimer's disease; and the starting population to further derive in vitro various committed neuronal progenitor populations such as proliferative TH-expressing neuronal cells.

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims. Thus, it is to be understood that variations in the present invention can be made without departing from the novel aspects of this invention as defined in the claims. All patents and articles cited herein are hereby incorporated by reference in their entirety and relied upon.

What is claimed is:

1. A method for obtaining a culture of human neural precursor cells capable of differentiating into neurons and glia comprising:
    a) culturing at least one neural precursor cell in a medium including a first mitogen selected from the group consisting of aFGF, bFGF, EGF, TGFα and combinations thereof;
    b) introducing into the neural precursor cell in the medium including the first mitogen a recombinant DNA construct comprising a receptor ligand-regulated c-myc cDNA, wherein c-myc cDNA is fused with DNA encoding a ligand-binding domain of a nuclear receptor; and
    c) expanding the neural precursor cell including the c-myc construct beyond thirty cell doublings prior to differentiation of said cell, wherein said expansion occurs in a medium containing the first mitogen and a second mitogen,
    wherein said second mitogen is selected from the group consisting of aFGF, bFGF, EGF, TGFα, serum and combinations thereof, and
    wherein said medium comprising the first mitogen and the second mitogen further comprises an amount of a c-myc-activating agent sufficient to maintain a stable cell line, wherein said c-myc-activating agent is capable of binding to the ligand-binding domain of said nuclear receptor.

2. The method of claim 1, wherein the neural precursor cell is derived from pluripotent embryonic stem cells.

3. The method of claim 1, wherein the neural precursor cell is derived from central nervous system tissue.

4. The method of claim 3, wherein the central nervous system tissue is selected from the group consisting of hippocampus, cerebral cortex, striatum, septum, hindbrain, and spinal cord.

5. The method of claim 1, wherein the second mitogen is different from the first mitogen.

6. The method of claim 1, wherein the nuclear receptor is selected from the group consisting of an estrogen receptor, an androgen receptor, a progesterone receptor, a glucocorticoid receptor, a thyroid hormone receptor, a retinoid receptor, and an ecdysone receptor.

7. The method of claim 1, wherein the c-myc-activating agent is selected from the group consisting of β-estradiol, RU38486, dexamethasone, thyroid hormones, retinoids, and ecdysone.

8. The method of claim 1, further comprising introducing a selectable marker into the neural precursor cell.

9. The method of claim 1, further comprising culturing the neural precursor cell in the presence of feeder cells.

10. The method of claim 9, wherein the feeder cells are selected from the group consisting of unmodified primary stem cells, immature glial cells, mature astrocytes, fibroblasts, neurons and mitotically-inhibited cells.

11. The method of claim 1, wherein the neural precursor cell is a cell of a clonal cell line.

12. The method of claim 1, wherein the neural precursor cell is capable of differentiating into a neuron upon withdrawing the mitogen and the c-myc activating agent.

13. A method of maintaining the capacity of a neural precursor cell line of a human to differentiate into neurons in vitro, wherein said cell line includes neural precursor cells capable of differentiating into neurons and glia, said method comprising:
    a) preparing a culture comprising at least one neural precursor cell from said neural precursor cell line, wherein said culture includes at least one mitogen selected from the group consisting of aFGF, bFGF, EGF, TGFα and combinations thereof;
    b) introducing into said neural precursor cell a recombinant DNA construct comprising a receptor ligand-regulated c-myc cDNA capable of expressing a chimeric c-myc protein fused with at least one nuclear receptor protein having a c-myc-activating ligand binding domain; and
    c) expanding the undifferentiated modified neural precursor cell beyond thirty cell doublings in a medium comprising said mitogen and an amount of a c-myc-activating agent.

14. The method of claim 13, wherein the neural precursor cell is derived from central nervous system tissue.

15. The method of claim 14, wherein the central nervous system tissue is selected from the group consisting of hippocampus, cerebral cortex, striatum, septum, hindbrain, and spinal cord.

16. The method of claim 13, wherein the nuclear receptor protein is selected from the group consisting of an estrogen receptor, an androgen receptor, a progesterone receptor, a glucocorticoid receptor, a thyroid hormone receptor, a retinoid receptor, and an ecdysone receptor.

17. The method of claim 13, wherein the c-myc-activating agent is selected from the group consisting of β-estradiol, RU38486, dexamethasone, thyroid hormones, retinoids, and ecdysone.

18. The method of claim 13, wherein said neural precursor cell line is a clonal cell line.

19. The method of claim 13, wherein the neural precursor cell is capable of differentiating into a neuron upon withdrawing the mitogen and the c-myc activating agent.

* * * * *

UNITED STATES PATENT AND TRADEMARK OFFICE
CERTIFICATE OF CORRECTION

| | | |
|---|---|---|
| PATENT NO. | : 7,544,511 B2 | Page 1 of 1 |
| APPLICATION NO. | : 10/047352 | |
| DATED | : June 9, 2009 | |
| INVENTOR(S) | : Yang et al. | |

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 200 days Delete the phrase "by 200 days" and insert -- by 689 days --

Signed and Sealed this

Twentieth Day of April, 2010

David J. Kappos
*Director of the United States Patent and Trademark Office*

(12) EX PARTE REEXAMINATION CERTIFICATE (8887th)
United States Patent
Yang et al.

(10) Number: US 7,544,511 C1
(45) Certificate Issued: *Mar. 6, 2012

(54) STABLE NEURAL STEM CELL LINE METHODS

(75) Inventors: Renji Yang, Silver Spring, MD (US); Karl K. Johe, Potomac, MD (US)

(73) Assignee: Neuralstem Biopharmaceuticals, Ltd., College Park, MD (US)

Reexamination Request:
No. 90/009,669, Mar. 4, 2010

Reexamination Certificate for:
Patent No.: 7,544,511
Issued: Jun. 9, 2009
Appl. No.: 10/047,352
Filed: Jan. 14, 2002

(*) Notice: This patent is subject to a terminal disclaimer.

Certificate of Correction issued Apr. 20, 2010.

Related U.S. Application Data

(63) Continuation of application No. 09/398,897, filed on Sep. 20, 1999, now abandoned, and a continuation-in-part of application No. 09/053,414, filed on Apr. 1, 1998, now abandoned, which is a continuation-in-part of application No. 08/719,450, filed on Sep. 25, 1996, now Pat. No. 5,753,506.

(60) Provisional application No. 60/101,354, filed on Sep. 22, 1998.

(51) Int. Cl.
*C12N 5/08* (2006.01)
*C12N 5/22* (2006.01)

(52) U.S. Cl. .................. 435/368; 435/375; 435/377
(58) Field of Classification Search ............... 435/368
See application file for complete search history.

(56) References Cited

To view the complete listing of prior art documents cited during the proceeding for Reexamination Control Number 90/009,669, please refer to the USPTO's public Patent Application Information Retrieval (PAIR) system under the Display References tab.

*Primary Examiner* — Sharon Turner

(57) ABSTRACT

A systematic and efficient method for establishing stable neural stem cell lines and neuronal progenitor lines is described. The resulting cell lines provide robust, simple, and reproducible cultures of human and other mammalian neurons in commercially useful mass quantities while maintaining normal karyotypes and normal neuronal phenotypes.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 5 and 13 are determined to be patentable as amended.

Claims 2-4, 6-12 and 14-19, dependent on an amended claim, are determined to be patentable.

1. A method for obtaining a culture of human neural precursor cells capable of differentiating into neurons and glia comprising:
    a) culturing at least one neural precursor cell in a medium including a first mitogen selected from the group consisting of aFGF, bFGF, EGF, TGFα and combinations thereof;
    b) introducing into the *at least one* neural precursor cell in the medium including the first mitogen a recombinant DNA construct comprising a receptor ligand-regulated c-myc cDNA, wherein c-myc cDNA is fused with DNA encoding a ligand-binding domain of a nuclear receptor; and
    c) expanding the neural precursor cell including the c-myc construct beyond thirty cell doublings prior to differentiation of said cell, wherein said expansion occurs in a medium containing the first mitogen and [a second mitogen,
    wherein said second mitogen is selected from the group consisting of aFGF, bFGF, EGF, TGFα,] serum [and combinations thereof], and
    wherein said medium comprising the first mitogen and the [second mitogen] *serum* further comprises an amount of a c-myc-activating agent sufficient to maintain a stable cell line, wherein said c-myc-activating agent is capable of binding to the ligand-binding domain of said nuclear receptor.

5. The method of claim 1, wherein the [second mitogen is different from the first mitogen] *serum is fetal bovine serum*.

13. A method of maintaining the capacity of a neural precursor cell line of a human to differentiate into neurons in vitro, wherein said cell line includes neural precursor cells capable of differentiating into neurons and glia, said method comprising:
    a) preparing a culture comprising at least one neural precursor cell from said neural precursor cell line, wherein said culture includes at least one mitogen selected from the group consisting of aFGF, bFGF, EGF, TGFα and combinations thereof;
    b) introducing into said neural precursor cell a recombinant DNA construct comprising a receptor ligand-regulated c-myc cDNA capable of expressing a chimeric c-myc protein fused with at least one nuclear receptor protein having a c-myc-activating ligand binding domain; and
    c) expanding the undifferentiated modified neural precursor cell beyond thirty cell doublings in a medium comprising said mitogen, *serum* and an amount of a c-myc-activating agent.

* * * * *